United States Patent
Forman (10) Patent No.: US 7,018,371 B2
(45) Date of Patent: Mar. 28, 2006

(54) COMBINATION IONIZING RADIATION AND RADIOSENSITIZER DELIVERY DEVICES AND METHODS FOR INHIBITING HYPERPLASIA

(75) Inventor: Michael R. Forman, Los Gatos, CA (US)

(73) Assignee: Xoft, Inc., Fremont, CA (US)

( * ) Notice: Subject to any disclaimer, the term of this patent is extended or adjusted under 35 U.S.C. 154(b) by 345 days.

(21) Appl. No.: 09/851,372

(22) Filed: May 7, 2001

(65) Prior Publication Data

US 2002/0165520 A1 Nov. 7, 2002

(51) Int. Cl.
- A61M 31/00 (2006.01)
- A61M 37/00 (2006.01)
- A61N 5/00 (2006.01)

(52) U.S. Cl. ............. 604/509; 604/103.01; 604/103.02; 604/103.08; 600/4; 600/3

(58) Field of Classification Search ............... 604/21, 604/22, 103.01, 103.02, 19, 20, 506–509, 604/93.01, 96.01, 103.06–103.08, 264, 523; 600/1–8, 103.06–103.08, 19–20, 506–509, 600/93.01, 96.01, 264, 523; 606/192, 194

See application file for complete search history.

(56) References Cited

U.S. PATENT DOCUMENTS

| | | |
|---|---|---|
| 3,976,071 A | 8/1976 | Sadek |
| 4,636,195 A | 1/1987 | Wolinsky |
| 4,832,686 A | 5/1989 | Anderson |
| 4,883,666 A | 11/1989 | Sabel et al. |
| 4,897,268 A | 1/1990 | Tice et al. |
| 5,059,166 A | 10/1991 | Fischell et al. |

(Continued)

FOREIGN PATENT DOCUMENTS

| | | |
|---|---|---|
| EP | 688580 | 6/1994 |
| EP | 593136 | 3/1997 |
| EP | 860180 | 8/1998 |
| EP | 633041 | 9/1999 |
| EP | 1057500 A1 | 6/2000 |

(Continued)

OTHER PUBLICATIONS

Choy, "Taxanes in combined–modality therapy for solid tumors" *Oncology* (1999) 13(10 Suppl.5):23–28 (abstract) [retrieved on Apr. 5, 2000]. Retrieved from :PMID: 10550824 UI: 20018487.

De Palo et al., "Concurrent radiotherapy and taxol as radiosensitizer in locally advanced or recurrent carcinoma of the uterine cervix. A pilot study" [online abstract], [retrieved on Apr. 13, 2000]. Retrieved from Internet.<URL: http://208.240.92.166/prof/me/html/98abstracts/gync/m_1404.htm> 1 page total.

(Continued)

*Primary Examiner*—Nicholas D. Lucchesi
*Assistant Examiner*—Catherine S. Williams (57) ABSTRACT

The present invention provides improved devices, methods, and kits for inhibiting restenosis and hyperplasia after intravascular intervention. In particular, the present invention provides controlled radiosensitizer delivery in combination with ionizing radiation to selected locations within a patient's vasculature to reduce and/or inhibit restenosis and hyperplasia rates with increased efficacy. In one embodiment, the combination radiation and radiosensitizer delivery catheter for inhibiting hyperplasia comprises a catheter body having a proximal end and distal end, an ionizing radiation source coupleable to the catheter body for applying a radiation dose to a body lumen, and a porous material, matrix, membrane, barrier, coating, infusion lumen, stent, graft, or reservoir for releasing an radiosensitizer to the body lumen.

32 Claims, 6 Drawing Sheets

U.S. PATENT DOCUMENTS

| | | | |
|---|---|---|---|
| 5,061,267 A | 10/1991 | Zeiher | |
| 5,090,043 A | 2/1992 | Parker et al. | |
| 5,163,952 A | 11/1992 | Froix | |
| 5,199,939 A | 4/1993 | Dake et al. | |
| 5,213,561 A | 5/1993 | Weinstein et al. | |
| RE34,421 E | 10/1993 | Parker et al. | |
| 5,256,141 A | 10/1993 | Gencheff et al. | |
| 5,282,785 A | 2/1994 | Shapland et al. | |
| 5,286,254 A * | 2/1994 | Shapland et al. | 604/21 |
| 5,302,168 A | 4/1994 | Hess | |
| 5,318,531 A * | 6/1994 | Leone | 604/103.01 |
| 5,342,348 A | 8/1994 | Kaplan | |
| 5,354,257 A | 10/1994 | Roubin et al. | |
| 5,411,466 A | 5/1995 | Hess | |
| 5,411,550 A | 5/1995 | Herweck et al. | |
| 5,419,760 A | 5/1995 | Narciso, Jr. | |
| 5,464,450 A | 11/1995 | Buscemi et al. | |
| 5,484,384 A | 1/1996 | Fearnot | |
| 5,484,584 A | 1/1996 | Wallace et al. | |
| 5,498,227 A | 3/1996 | Mawad | |
| 5,500,013 A | 3/1996 | Buscemi et al. | |
| 5,503,613 A | 4/1996 | Weinberger | |
| 5,505,613 A | 4/1996 | Krummenacher | |
| 5,540,659 A | 7/1996 | Teirstein | |
| 5,543,158 A | 8/1996 | Gref et al. | |
| 5,545,208 A | 8/1996 | Wolff et al. | |
| 5,551,954 A | 9/1996 | Buscemi et al. | |
| 5,566,221 A | 10/1996 | Smith et al. | |
| 5,569,198 A | 10/1996 | Racchini | |
| 5,591,227 A | 1/1997 | Dinh et al. | |
| 5,609,629 A | 3/1997 | Fearnot et al. | |
| 5,616,114 A | 4/1997 | Thornton et al. | |
| 5,618,266 A | 4/1997 | Liprie | |
| 5,624,372 A | 4/1997 | Liprie | |
| 5,637,113 A | 6/1997 | Tartaglia et al. | |
| 5,643,171 A | 7/1997 | Bradshaw et al. | |
| 5,649,977 A | 7/1997 | Campbell | |
| 5,653,736 A | 8/1997 | Glastra | |
| 5,656,297 A | 8/1997 | Bernstein et al. | |
| 5,679,400 A | 10/1997 | Tuch | |
| 5,681,558 A | 10/1997 | Johns et al. | |
| 5,700,286 A | 12/1997 | Tartaglia et al. | |
| 5,704,908 A | 1/1998 | Hofmann et al. | |
| 5,735,811 A | 4/1998 | Brisken | |
| 5,769,883 A | 6/1998 | Buscemi et al. | |
| 5,772,642 A | 6/1998 | Ciamacco, Jr. et al. | |
| 5,800,392 A | 9/1998 | Racchini | |
| 5,837,008 A | 11/1998 | Berg et al. | |
| 5,843,172 A | 12/1998 | Yan | |
| 5,851,231 A | 12/1998 | Wolff et al. | |
| 5,863,285 A | 1/1999 | Coletti | |
| 5,876,452 A | 3/1999 | Athanasiou et al. | |
| 5,891,108 A | 4/1999 | Leone et al. | |
| 5,893,840 A | 4/1999 | Hull et al. | |
| 5,945,439 A * | 8/1999 | Richter et al. | 514/410 |
| 5,947,889 A | 9/1999 | Hehrlein | |
| 5,951,458 A * | 9/1999 | Hastings et al. | 600/3 |
| 5,951,586 A | 9/1999 | Berg et al. | |
| 5,968,092 A | 10/1999 | Buscemi et al. | |
| 5,971,909 A | 10/1999 | Bradshaw et al. | |
| 5,972,027 A | 10/1999 | Johnson | |
| 5,980,551 A | 11/1999 | Summers et al. | |
| 5,980,566 A | 11/1999 | Alt et al. | |
| 5,985,307 A | 11/1999 | Hanson et al. | |
| 5,993,374 A | 11/1999 | Kick | |
| 5,997,468 A | 12/1999 | Wolff et al. | |
| 6,001,054 A * | 12/1999 | Regulla et al. | 600/1 |
| 6,063,101 A | 5/2000 | Jacobsen et al. | |
| 6,069,938 A | 5/2000 | Chornenky et al. | |
| 6,071,305 A | 6/2000 | Brown et al. | |
| 6,072,038 A | 6/2000 | Sessler et al. | |
| 6,095,966 A | 8/2000 | Chornenky et al. | |
| 6,099,561 A | 8/2000 | Alt | |
| 6,108,402 A | 8/2000 | Chornenky | |
| 6,149,574 A | 11/2000 | Trauthen et al. | |
| 6,176,842 B1 * | 1/2001 | Tachibana et al. | 604/22 |
| 6,183,409 B1 | 2/2001 | Armini | |
| 6,200,257 B1 * | 3/2001 | Winkler | 600/3 |
| 6,210,393 B1 | 4/2001 | Brisken | |
| 6,390,967 B1 * | 5/2002 | Forman et al. | 600/3 |
| 6,398,709 B1 | 6/2002 | Ehr et al. | |
| 6,400,796 B1 | 6/2002 | Munro, III et al. | |
| 6,537,195 B1 * | 3/2003 | Forman | 600/3 |

FOREIGN PATENT DOCUMENTS

| | | |
|---|---|---|
| JP | 2000-279524 A | 10/2000 |
| WO | WO 96/13303 | 5/1996 |
| WO | WO 96/14898 | 5/1996 |
| WO | WO 96/23543 | 8/1996 |
| WO | WO 97/07740 | 3/1997 |
| WO | WO 98/36790 | 8/1998 |
| WO | WO 99/51299 | 10/1999 |
| WO | WO 99/55285 | 11/1999 |
| WO | WO 00/00238 | 1/2000 |
| WO | WO 00/47197 | 8/2000 |
| WO | WO 00/70645 | 11/2000 |
| WO | WO 01/93778 A1 | 12/2001 |

OTHER PUBLICATIONS

Enzinger et al., "Phase I/II neoadjuvant concurrent 96 hour taxol, cisplatin, and radiation therapy: Promising toxicity profile and response in localized esophageal cancer" [online abstract], [retrieved on Mar. 19, 2000]. Retrieved from Internet. <URL: http://www.asco.org/prof/me/html/99 abracts/gic/m__1038.htm> 1 page total.

Kessler et al., "Effects of human interferons and 60 cobalt radiation on canine and feline tumour cells–preclinical studies" [online], [retrieved on May 18, 2000]. Retrieved from Internet. <URL: http://130.14.32.42/cgi–bin/VERSION__A/IGM–cient?15504+records+161>Source: *Zentralbl. Veterinarmed. A.* (1996) 43(10):599–609. 1 page total.

Lederman, "Combining chemotherapy and radiation" [online], [retrieved on Apr. 5, 2000]. Retrieved from Internet. <URL: http://www.siuh.edu/radoncology/charticle3.html> 2 pages total.

Wright, "Molecular radiosensitizers target proliferation and apoptosis pathways in tumour cells" *Oncology* (2000) 45(11):4 pages total.

Schmidberger et al., "The combined effect of interferon beta and radiation on five human tumor cell lines and embryonal lung fibroblasts" [online abstract], [retrieved on May 18, 2000]. Retrieved from Internet. <URL: http://130.14.32.42/cgi–bin/VERSION__A/IGM–cient?15504+records+61> Source: *Int. J. Radiat. Oncol. Biol. Phys.* (1999) 43(2):405–412. 1 page total.

SCVIR Meeting, San Francisco, CA, Mar. 2, 1998, "Taxol may help prevent blood vessels from re–clogging" [online], [retrieved on Mar. 19, 2000]. Retrieved from Internet. <URL: plsgroup.com/dg/5e37a.htm> 3 pages total.

* cited by examiner

COMBINATION IONIZING RADIATION AND RADIOSENSITIZER DELIVERY DEVICES AND METHODS FOR INHIBITING HYPERPLASIA

BACKGROUND OF THE INVENTION

1. Field of Invention

The present invention relates generally to medical devices and methods for inhibiting restenosis in a blood vessel after an initial treatment for opening a stenotic region in a blood vessel. More particularly, the present invention relates to combination radiation and radiosensitizer delivery devices for inhibiting hyperplasia following balloon angioplasty and other interventional treatments.

A number of percutaneous intravascular procedures have been developed for treating stenotic atherosclerotic regions of a patient's vasculature to restore adequate blood flow. The most successful of these treatments is percutaneous transluminal angioplasty (PTA). In PTA, a catheter, having an expansible distal end usually in the form of an inflatable balloon, is positioned in the blood vessel at the stenotic site. The expansible end is expanded to dilate the vessel to restore adequate blood flow beyond the diseased region. Other procedures for opening stenotic regions include directional atherectomy, rotational atherectomy, laser angioplasty, stenting, and the like. While these procedures have gained wide acceptance (either alone or in combination, particularly PTA in combination with stenting), they continue to suffer from significant disadvantages. A particularly common disadvantage with PTA and other known procedures for opening stenotic regions is the frequent occurrence of restenosis.

Restenosis refers to the re-narrowing of an artery after an initially successful angioplasty. Restenosis afflicts approximately up to 50% of all angioplasty patients and is the result of injury to the blood vessel wall during the lumen opening angioplasty procedure. In some patients, the injury initiates a repair response that is characterized by smooth muscle cell proliferation referred to as "hyperplasia" in the region traumatized by the angioplasty. This proliferation of smooth muscle cells re-narrows the lumen that was opened by the angioplasty within a few weeks to a few months, thereby necessitating a repeat PTA or other procedure to alleviate the restenosis so that blood perfusion may be restored.

A number of strategies have been proposed to treat hyperplasia and reduce restenosis. Previously proposed strategies include prolonged balloon inflation during angioplasty, treatment of the blood vessel with a heated balloon, stenting of the region, use of radiotherapy to treat in-stent restenosis, the administration of therapeutic drugs following angioplasty, and other procedures. While these proposals have enjoyed varying levels of success, no one of these procedures is proven to be entirely successful in completely avoiding all occurrences of restenosis and hyperplasia.

As an alternative to the above mentioned therapies, the combination of radioisotope radiation and drug therapy following PTA for the inhibition of hyperplasia has also been proposed. Drug therapy infuses or releases a drug through a catheter or from a stent, while intravascular radiotherapy may configure catheters, guidewires, and stents to position a solid radioisotopic source (such as a wire, strip, pellet, seed, bead, or the like). While combination delivery of therapeutic agents with radioisotopic sources holds promise, optimum combinations of drugs and radiation have yet to be identified.

For these reasons, it would be desirable to provide improved devices and methods for inhibiting restenosis and hyperplasia following angioplasty and other interventional treatments. In particular, it would be desirable to provide improved devices, methods, and kits for delivery of new and optimum drugs in combination with ionizing radiation to a blood vessel to reduce and/or inhibit restenosis and hyperplasia rates with increased efficacy. It would further be desirable to provide such devices and methods which significantly reduce dose concentrations of the drugs and/or radiation within the vessel wall while delivering sufficiently uniform radiation dosages and promoting endothelialization of the vessel wall. At least some of these objectives will be met by the devices and methods of the present invention described hereinafter.

2. Description of Background Art

Full descriptions of exemplary x-ray sources for use in the present invention are described in co-pending U.S. patent application Ser. No. 09/299,304, assigned to the assignee herein, and U.S. Pat. No. 6,095,966, licensed to the assignee herein. Devices and methods for exposing intravascular and other treatment locations to radioisotopic materials in combination with therapeutic drugs are described in the following: U.S. Pat. Nos. 6,149,574; 5,993,374; 5,951,458; and International Publication Nos. WO 00/47197; WO 00/00238; WO 99/55285; WO 99/51299; WO 98/36790; and WO 96/23543. The use of texaphyrins for radiation sensitization is described in U.S. Pat. No. 6,072,038. Devices and methods for exposing intravascular locations to radioactive materials are described in the following: U.S. Pat. Nos. 6,069,938; 5,971,909; 5,653,736; 5,643,171; 5,624,372; 5,618,266; 5,616,114; 5,540,659; 5,505,613; 5,503,613; 5,498,227; 5,484,384; 5,411,466; 5,354,257; 5,302,168; 5,256,141; 5,213,561; 5,199,939; 5,061,267; and 5,059,166, European applications 860 180; 688 580; 633 041; and 593 136, and International Publications WO 97/07740; WO 96/14898; and WO 96/13303. Drug delivery within the vasculature is described in U.S. Pat. Nos. 6,099,561; 6,071,305; 6,063,101; 5,997,468; 5,980,551; 5,980,566; 5,972,027; 5,968,092; 5,951,586; 5,893,840; 5,891,108; 5,851,231; 5,843,172; 5,837,008; 5,769,883; 5,735,811; 5,700,286; 5,681,558; 5,679,400; 5,649,977; 5,637,113; 5,609,629; 5,591,227; 5,551,954; 5,545,208; 5,500,013; 5,464,450; 5,419,760; 5,411,550; 5,342,348; 5,286,254; and 5,163,952. Biodegradable materials are described in U.S. Pat. Nos. 5,876,452; 5,656,297; 5,543,158; 5,484,584; 4,897,268; 4,883,666; 4,832,686; and 3,976,071.

The disclosure of this application is related to the disclosures of the following co-pending applications being filed on the same day: U.S. patent application Ser. Nos. 09/850,721 and 09/850,728.

The full disclosures of each of the above references are incorporated herein by reference.

SUMMARY OF THE INVENTION

The present invention provides improved devices, methods, and kits for inhibiting restenosis and hyperplasia after intravascular intervention. In particular, the present invention provides controlled radiosensitizer delivery in combination with ionizing radiation delivery to selected locations within a patient's vasculature to reduce and/or inhibit restenosis and hyperplasia rates with increased efficacy. The methods and apparatus of the present invention can significantly reduce dose concentrations of radiosensitizers and/or radiation within the vessel wall while delivering sufficiently uniform radiation dosages and promoting endothelialization of the vessel wall.

The term "intravascular intervention" includes a variety of corrective procedures that may be performed to at least partially resolve a stenotic condition. Usually, the corrective procedure will comprise balloon angioplasty. The corrective procedure could also comprise atherectomy, rotational atherectomy, laser angioplasty, stenting, or the like, where the lumen of the treated blood vessel is enlarged to at least partially alleviate a stenotic condition which existed prior to the treatment. The corrective procedure could also involve coronary artery bypass, vascular graft implantation, endarterectomy, or the like.

By "controlled" radiosensitizer delivery, it is meant that a predetermined amount of the radiosensitizer is released or delivered at a predetermined rate to a blood vessel. Typically, such controlled delivery maintains a steady-state concentration of the radiosensitizer in a vascular environment within a desired therapeutic range of time, e.g. hours, days, weeks, or in some cases months.

In a first aspect of the present invention, a combination radiation and radiosensitizer delivery catheter for inhibiting hyperplasia generally comprises a catheter body having a proximal end and distal end, a ionizing radiation source coupleable to the catheter body for applying a radiation dose to a body lumen, and means coupleable to the catheter body or the radiation source for releasing a radiosensitizer to the body lumen. The body lumen may be any blood vessel in the patient's vasculature, including veins, arteries, aorta, and particularly including peripheral and coronary arteries.

The ionizing radiation source is preferably an x-ray tube since it provides many advantages, such as convenient dosing where the source may be easily turned on and off, minimal disposal problems, and the like. Alternatively, the ionizing radiation source may comprise a radioisotope, such as a solid radioisotopic source (e.g., wire, strip, pellet, seed, bead, or the like), or a liquid radioisotopic filled balloon. In the latter case, the balloon has been specially configured to prevent leakage of the radioisotopic material from the balloon into the body lumen or blood stream. Still further, the ionizing radiation source may comprise a receptacle in the catheter body for receiving radioisotopic materials like pellets or liquids. The radioisotopic material may be selected to emit alpha, beta, or gamma radiation. Usually, alpha and beta radiation are preferred since they may be quickly absorbed by surrounding tissue and will not penetrate substantially beyond the wall of the body lumen being treated. Accordingly, incidental irradiation of the heart and other organs adjacent to the treatment region can be substantially eliminated.

The means may comprise a source of at least one radiosensitizer selected from the group consisting of taxol, misonidazole, metronidazole, etanidazole, 5-fluorouracil, texaphyrin, C225 (an anti-EGFR monoclonal antibody), and cyclooxygenase-2 inhibitor. The radiosensitizer may also be a prodrug (e.g., precursor substances that are converted into an active form in the body) of any of the above described radiosensitizers. More preferably, the means comprises a source of taxol, incorporated in a solution with polyoxyethylated castor oil and dehydrated alcohol. The radiosensitizer may also be attached or encapsulated in a lipid or surfactant carrier.

The combination of radiosensitizers and radiation therapy reduces and/or inhibits restenosis and hyperplasia rates with increased efficiency. In some instances, at least, it will be expected that the radiation will provide an immediate inhibition of cell proliferation while the radiosensitizers, which may be released over relatively long periods of time, e.g. days, weeks, or in some cases months, will provide prolonged inhibition. The delivery of radiosensitizers is particularly advantageous since radiosensitizers provide synergistic enhancement to radiation effects, such as enhancing apoptosis of proliferative smooth muscle cells and/or minimizing smooth muscle cell proliferation. In particular, radiosentizers may enhance the effect of radiation by increasing the cell cycle in which proliferative smooth muscle cells are most susceptible to radiation. Moreover, radiosentizers may inhibit radiation DNA damage repair of proliferative smooth muscle cells to further reduce and/or inhibit restenosis and hyperplasia. It will be appreciated that many of the above described radiosensitizers may also promote endothelialization of the vessel wall, which is needed for healing. Furthermore, a combined balance of both therapies allows for reduced dosages/concentrations of radiation and/or radiosensitizers in the body lumen, as compared to relying on a single therapy with an increased dosage which may not be as effective.

It will be appreciated that there are a number of means available for releasing any of the above described radiosensitizers. Conventional intravascular delivery devices typically comprise a source of the radiosensitizer, that may be external or internal to the device, and means for controlled radiosensitizer release to the body lumen. Such means may comprise a porous material which contains the radiosensitizer, wherein the radiosensitizer may elute out at a controlled rate from the pores. Such means may alternatively comprise a matrix, membrane, barrier, or coating which includes the radiosensitizer. Usually, such a matrix comprises a rate controlling material wherein the rate controlling material controls the rate at which the radiosensitizer is released from the matrix. Such means may further comprise an infusion lumen for radiosensitizer release or a radiosensitizer eluting stent or graft. Still further, such means may comprise a reservoir containing the radiosensitizer and a cover over the reservoir. Typically, the cover comprises a matrix, membrane, or barrier which in turn controls the rate at which the radiosensitizer is released from the reservoir.

In one embodiment, the means for releasing the radiosensitizer may comprise at least one microporous balloon on the catheter body. It is presently preferred that such a one balloon embodiment be employed in the coronary arteries as these vessels are relatively limited in size. The microporous balloon is usually inflated with any of the above described radiosensitizers and the radiosensitizer is released at a controlled rate from the microporous balloon by elution from pores. The microporous balloon is preferably elastic and made from nylon, Pebax, polyurethane, or like materials. The ionizing radiation source is typically positionable within the balloon.

In another embodiment, the means for releasing the radiosensitizer may comprise a matrix, membrane, barrier, or coating formed over at least a portion of at least one balloon on the catheter body. The radiosensitizer may be disposed in the matrix or on a surface of the balloon beneath the matrix and the ionizing radiation source is typically positionable within the balloon. The matrix will typically comprise a rate controlling material, wherein the rate controlling material controls the rate at which the radiosensitizer is released from or through the matrix. The rate controlling material may be composed of degradable, partially degradable, nondegradable polymer, synthetic, or natural material. The matrix may degrade by bulk degradation, in which the matrix degrades throughout, or preferably by surface degradation, in which a surface of the matrix degrades over time while maintaining bulk integrity, to allow release of the radiosensitizer. Alternatively, a nondegradable matrix may release the radiosensitizer by diffusion through the matrix. Optionally, the rate controlling material may be porous so as to allow elution of the radiosensitizer from pores.

In a further embodiment, the means may comprise a matrix, membrane, barrier, or coating formed over at least a portion of a radioisotopic balloon, wherein the radiosensitizer is in or beneath the matrix. The matrix may allow for controlled release of the radiosensitizer into the body lumen in a variety of forms as described above. Additionally, the liquid radioisotope filled balloon will serve as the ionizing radiation source.

Any of the above described balloons may further comprise perfusion threading on an outer surface to allow for blood perfusion. Such threading may form a spiral, helical, or angled pattern on the balloon surface. The catheter of the present invention may alternatively be equipped with a perfusion lumen/port to permit blood flow past the balloon when inflated.

In a second aspect of the present invention, a combined radiation and radiosensitizer delivery catheter for inhibiting hyperplasia generally comprises a catheter body having an infusion lumen for releasing a radiosensitizer, a pair of axially spaced apart balloons on the catheter body, and an ionizing radiation source. The ionizing radiation source applies a radiation dose between the axially spaced apart balloons while the infusion lumen releases the radiosensitizer therein. It is presently preferred that such a two balloon catheter embodiment be employed in the peripheral arteries as such a structure may help center and correctly position the radiation source in the peripheral vessels, provide a pocket for drug delivery, and aid in uniform radiation dosimetry, as described in greater detail in co-pending U.S. patent application Ser. No. 09/653,444, assigned the assignee herein, the full disclosure of which is incorporated herein by reference.

In a third aspect of the present invention, methods for inhibiting hyperplasia in a body lumen are provided. One method includes releasing a radiosensitizer at a target region within the body lumen and directing ionizing radiation at the target region, wherein the radiosensitizer and radiation combine to inhibit hyperplasia. The "target region" will be a length within a blood vessel which is at risk of hyperplasia, typically as a result of the initial intravascular intervention(s). The method may further comprise inflating a balloon at the target region, wherein the radiosensitizer is released from the balloon. The balloon may be inflated with the radiosensitizer so that the radiosensitizer is released from an interior of the balloon through pores or the radiosensitizer may be released from a surface of the balloon through a rate controlling matrix. The method may optionally comprise isolating the target region, wherein the radiosensitizer is released into the isolated region. The isolating may comprises inflating a pair of axially spaced apart balloons or expanding a pair of axially spaced apart mechanical barriers. Typically, the ionizing radiation source is positioned within the balloon or the isolated target region. The ionizing radiation source may comprise an x-ray tube, wherein positioning generally comprises energizing the x-ray tube and translating the x-ray tube to traverse the target region. Alternatively, the ionizing radiation source may comprise a radioisotope or a receptacle in the catheter body. The ionizing radiation source generally applies a total radiation dose in a range from about 4 Gy to 24 Gy, preferably from 14 Gy to 20 Gy. The total amount of radiosensitizer released will typically depend on the specific radiosensitizer being delivered. The radiation dose and radiosensitizer release may additionally be carried out simultaneously or sequentially.

In a fourth aspect of the present invention, kits comprising a catheter and instructions on how to use the catheter are provided. The kit may also include a source of the radiosensitizer. The catheter may comprise any of the delivery structures described herein, while the instructions for use will generally recite the steps for performing one or more of the above described methods. The instructions will often be printed, optionally being at least in-part disposed on packaging. The instructions may alternatively comprise a videotape, a CD-ROM or other machine readable code, a graphical representation, or the like showing any of the above described methods.

DESCRIPTION OF THE SPECIFIC EMBODIMENTS

The present invention provides improved devices, methods, and kits for inhibiting restenosis and hyperplasia after intravascular intervention. In particular, the present invention provides controlled radiosensitizer delivery in combination with ionizing radiation delivery to selected locations within a patient's vasculature to reduce and/or inhibit restenosis and hyperplasia rates with increased efficacy.

Figure 1:
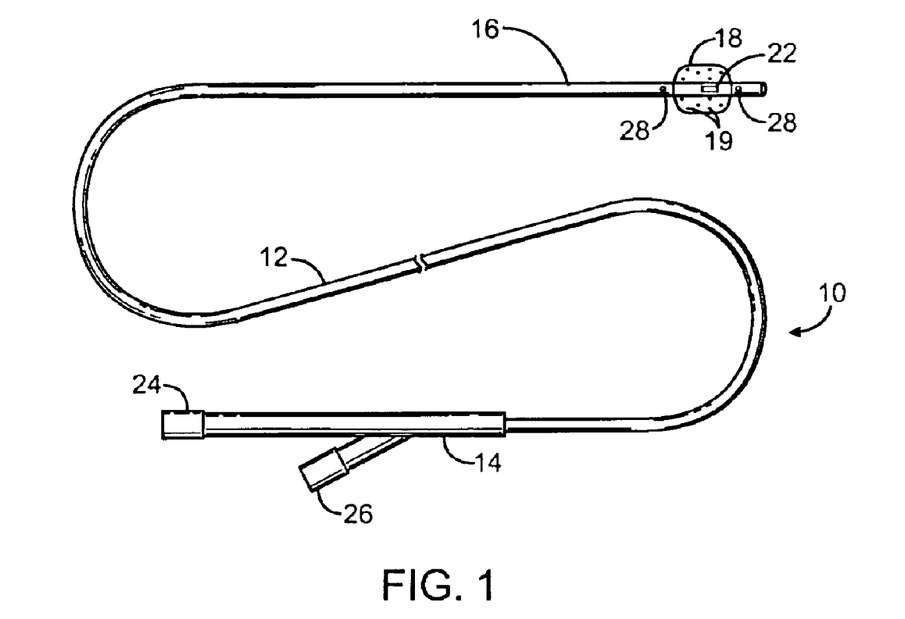
FIG. 1 is a plan view of an apparatus according the present invention.
Figure 2:
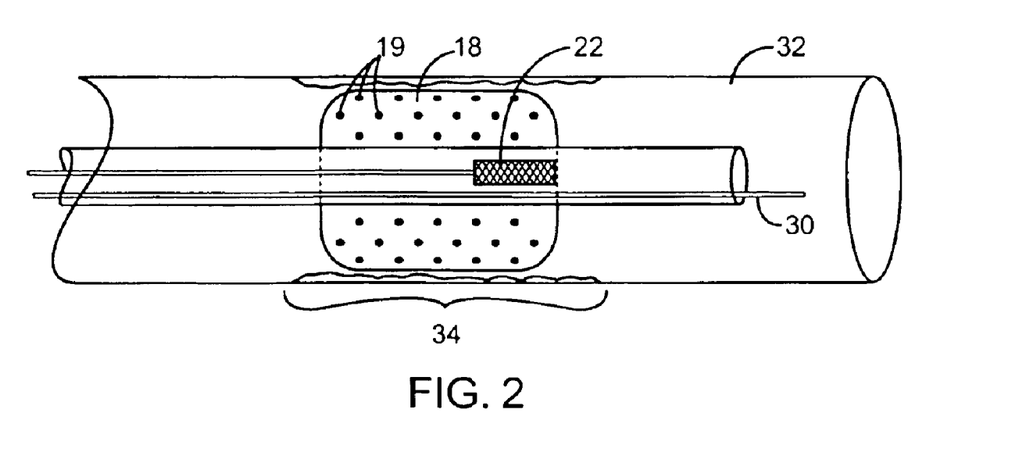
FIG. 2 is a cross sectional view of the apparatus of FIG. 1 within a blood vessel.

FIGS. 1 and 2 illustrate a combination radiation and radiosensitizer delivery catheter 10 constructed in accordance with the principles of the present invention. The combination radiation and radiosensitizer delivery catheter 10 comprises a shaft or body 12 having a proximal end 14 and distal end 16, a radiation source 22 coupleable to the distal end 16 of the catheter body 12 for applying a radiation dose to a target region 34 in a body lumen 32, and means coupleable to the distal end 16 of the catheter body 12 for releasing a radiosensitizer 19 to the target region 34. The proximal end 14 of shaft 12 includes a guidewire lumen luer fitting 24 and a balloon luer fitting 26. The guidewire luer fitting 24 is in fluid communication with a guidewire/perfusion lumen that is in turn in fluid communication with perfusion ports 28. Perfusion ports 28 are well known in the art as a means of permitting some blood flow past a balloon 18 that is inflated or otherwise blocking a blood vessel. The balloon luer fitting 26 is in fluid communication with a balloon inflation lumen that is in turn in fluid communication with balloon 18. It will be appreciated that the following depictions are for illustration purposes only and does not necessarily reflect the actual shape, size, or distribution of the delivery catheter 10.

The body lumen 32 may be any blood vessel in the patient's vasculature, including veins, arteries, aorta, and particularly including peripheral and coronary arteries. It will be appreciated that the present invention may also find use in body lumens 32 other than blood vessels. For example, the present invention may be applied to many internal corporeal tissue organs, such as organs, nerves, glands, ducts, and the like.

The radiation source 22 may be a radioisotope or a receptacle for receiving radioisotopic materials. Radioisotope sources may comprise a point source, wire, strip, pellet, seed, bead, liquid radioisotope balloon, and the like, selected to emit alpha, beta, or gamma radiation. In an exemplary embodiment, the radiation source 22 is an x-ray tube, as illustrated in FIGS. 1 and 2. The x-ray tube 22 can be isotropic, such as a transmission anode, or non-isotropic, such as an opaque anode. The x-ray will typically operate at an energy in the range from 18 kV to 28 kV. Exemplary x-ray sources are described in co-pending application Ser. No. 09/299,304, assigned to the assignee herein, and U.S. Pat. No. 6,095,966, licensed to the assignee herein. Other suitable x-ray sources are described in U.S. Pat. Nos. 6,134,300 and 5,428,658, and U.S. Pat. No. 34,421, the full disclosures of which are incorporated herein by reference. The total amount of radiation applied depends in part on the level and amount of vessel injury, as well as the total amount of radiosensitizer delivered, and will typically be in a range from about 4 Gy to 24 Gy, preferably from 14 Gy to 24 Gy. As described above, an x-ray tube 22 is preferable as it provides many advantages, such as, convenient dosing where the source may be easily turned on and off, eliminates the need to prepare, handle, and dispose of radioisotopes, and the like.

Suitable radiosensitizers 19 include taxol, misonidazole, metronidazole, etanidazole, 5-fluorouracil, texaphyrin (e.g., Xcytrin™ sold commercially by Pharmacyclics, and RSR13™ sold commercially by Allos Therapeutics), C225, and cyclooxygenase-2 inhibitor. The radiosensitizer 19 may also be a prodrug of any of the above described radiosensitizers. Preferably, the radiosensitizer 19 comprises taxol, alone or in combination with any of the other radiosensitizers described above. The total amount of radiosensitizer released depends on the specific radiosensitizer being delivered as well as on the level and amount of vessel injury and the total amount of radiation applied. For example, taxol may be released at levels of 130 micrograms/cm$^3$ or less.

The combination of radiosensitizers 19 and radiation 22 reduces and/or inhibits restenosis and hyperplasia rates with increased efficiency. The delivery of radiosensitizers 19 is particularly advantageous since radiosensitizers provide synergistic enhancement to radiation effects, such as enhancing apoptosis of proliferative smooth muscle cells and/or minimizing smooth muscle cell proliferation. It will be appreciated that many of the above described radiosensitizers 19 may also promote endothelialization of the vessel wall, which is needed for healing. Moreover, a combined balance of both therapies allows for reduced dosages/concentrations of radiation and/or radiosensitizers in the body lumen, as compared to relying on a single therapy with an increased dosage.

Figure 3A:
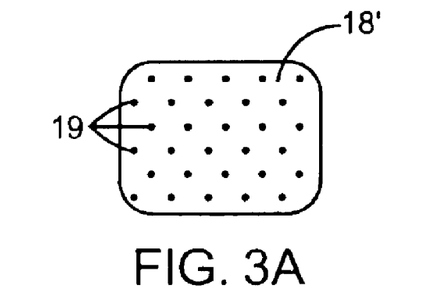
FIGS. 3A–3C illustrate various means for releasing a radiosensitizer.

Referring now to FIGS. 2 and 3A, the means for releasing the radiosensitizer may comprise at least one microporous balloon 18 on the catheter body 12. It is presently preferred that such a one balloon embodiment be employed in the coronary arteries. The microporous balloon 18 is usually inflated with any of the above described radiosensitizers 19 via the balloon luer fitting 26. The radiosensitizer 19 is then released from the microporous balloon 18 by elution from pores. The microporous balloon 18 is preferably elastic and made from nylon, Pebax, polyurethane, or like materials, and may be an integral extension of the catheter body 12, or attached to the distal end 16 of the catheter body 12 by suitable adhesives, heat welding, or the like. The catheter body 12 may be formed from conventional materials, such as polyethylenes, polyimides, and copolymers and derivatives thereof.

Figure 3B:
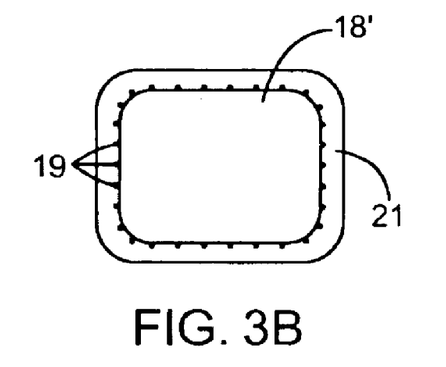
Figure 3C:
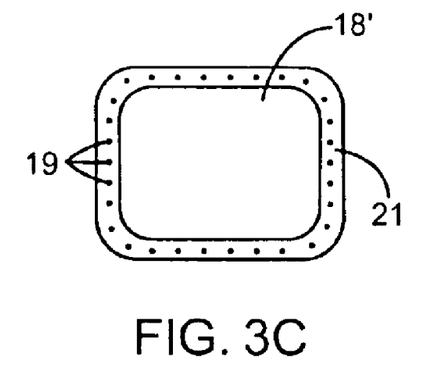

Referring now to FIGS. 3B and 3C, alternative means for releasing the radiosensitizer may comprise a matrix 21 formed over at least a portion of a balloon 18' on the catheter body 12. The matrix 21 will typically comprise a rate controlling material, wherein the rate controlling material controls the rate at which the radiosensitizer 19 is released from or through the matrix 21. The radiosensitizer 19 may be disposed on a surface of the balloon 18', as illustrated in FIG. 3B, or within the matrix 21, as illustrated in FIG. 3C. The balloon 18' may be inelastic or preferably elastic, and is preferably made of polyurethane, Pebax, or other medical grade elastomeric material suitable for constructing puncture-resistant elastic balloons. Balloon 18' is generally inflatable via the balloon luer fitting 26. The rate controlling material may comprise degradable, partially degradable, nondegradable polymer, synthetic, or natural material. The matrix may degrade by bulk degradation, in which the matrix degrades throughout, or preferably by surface degradation, in which a surface of the matrix degrades over time while maintaining bulk integrity, to allow release of the radiosensitizer. Alternatively, a nondegradable matrix may release the radiosensitizer by diffusion through the matrix. Optionally, the rate controlling material may be porous so as to allow elution of the radiosensitizer from pores. Typically, the radiosensitizer 19 and/or the matrix 21 are coated, sprayed, dipped, deposited, or painted on the balloon surface.

Figure 4:
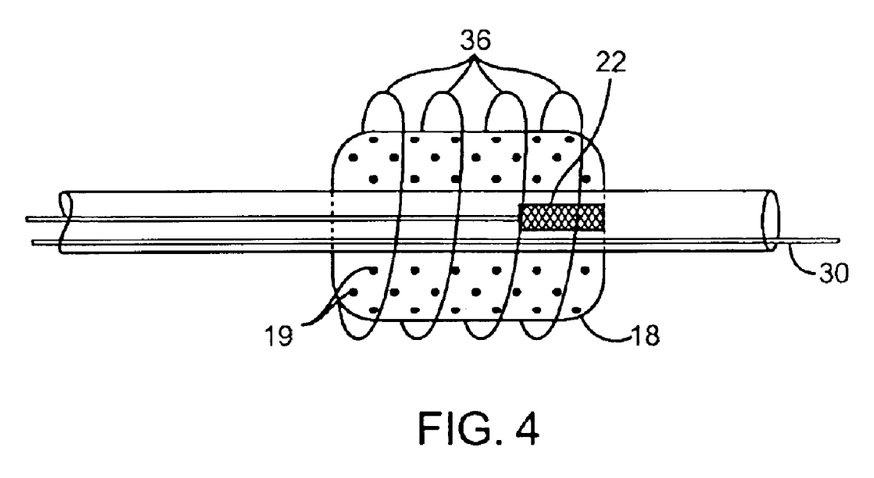
FIG. 4 illustrates a distal tip of the catheter of FIG. 1 with a spiral perfusion balloon.

Referring now to FIG. 4, in some instances, any of the above described balloons may further incorporate a perfusion threading or band 36 affixed to an outer surface of the balloon 18 by adhesion bonding, heat welding, fasteners, or the like. Threading patterns may be spiral (as shown in FIG. 4), helical, or angled. The threading 36 may be formed from polymer materials and may aid in perfusion so as to permit blood flow past the balloon when inflated.

In operation, an appropriately sized catheter 10 as illustrated in FIGS. 1 and 2 is advanced via a guidewire 30 within a blood vessel segment 32 having a treatment region 34 so that the radiation source 22 (which is positionable within the balloon 18) and the at least one balloon 18 are positioned at the target region 32. The treatment region 34 has previously been enlarged by balloon angioplasty or other procedures such that atherosclerotic plaque has been radially compressed by expansion of the balloon portion of an angioplasty device (not shown). The balloon 18 (as shown in FIG. 2) is inflated in the blood vessel via the balloon luer fitting 26 and the x-ray tube 22 is turned on and energized. The radiosensitizer 19 is then released to the target region 34 by any of the means described above while the x-ray tube 22 is translated along an axial line through a center of the balloon 18 to direct an x-ray radiation dose to the target region 34. The radiation and radiosensitizer delivery is carried out for a predetermined period of time calculated to deliver an effective dosage/concentration to the wall of the blood vessel to inhibit hyperplasia. Moreover, radiation and radiosensitizer delivery may be carried out simultaneously or sequentially.

Figure 5:
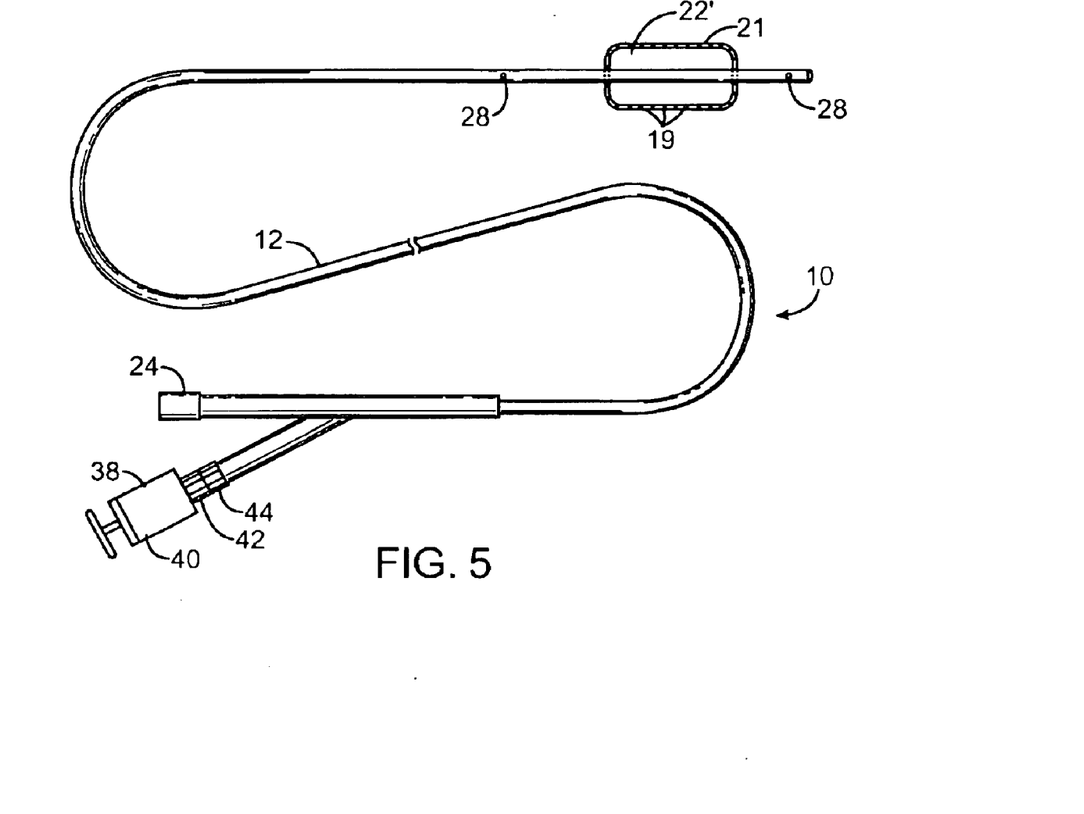
FIG. 5 is a plan view of an alternate embodiment of an apparatus according to the present invention.
Figure 6:
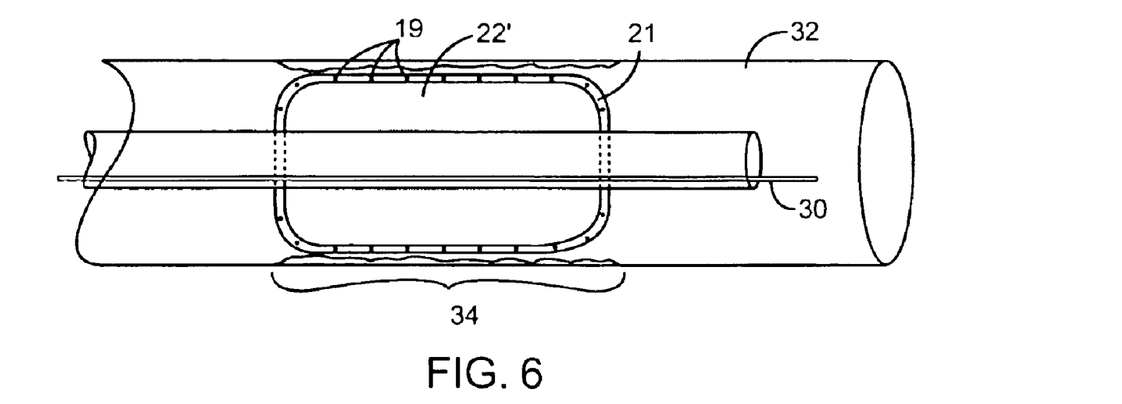
FIG. 6 is a cross sectional view of the apparatus of FIG. 5 within a blood vessel.

Referring now to FIGS. 5 and 6, an alternative embodiment of an apparatus according to the present invention is illustrated. The combination radiation and radiosensitizer delivery catheter 10 comprises a shaft or body 12, a radioisotopic balloon 22' coupleable to the catheter body 12 for applying a radiation dose to a target region 34 in a body lumen 32, and a matrix 21 coupleable to the radioisotopic balloon 22' for releasing a radiosensitizer 19 to the target region 34. The radioisotopic balloon 22' is an elastic or preferably an inelastic balloon, which may preferably be made from polyethylene terephthalate (PET), polyvinyl chloride (PVC), or other medical grade material suitable for constructing a strong non-compliant balloon.

A shielded injector 38, which may be a manual or automated syringe containing a radioisotopic liquid 40, or a pump connected to a reservoir of radioisotopic liquid 40, is connected to the proximal end of shaft 12. Shielded injector 38 is in fluid communication with a radioisotopic inflation lumen, which in turn is in fluid communication with radioisotopic balloon 22' via radioisotopic inflation lumen ports. To prevent possible spillage and corresponding radioisotopic contamination of the operating room and/or its personnel, the shielded injector 38 is equipped with a fail-safe non-detachable connector 42, which cannot be detached from the corresponding receptacle 44 of shaft 12 once it is attached thereto. Non-detachable connector 42 also prevents the radioisotopic fluid 40 from being discharged from injector 38 until the connector is connected to the receptacle in shaft 12. Connectors having ring-detents and other non-detachable fluid fittings are well known in the art, as are piercing valves and other common methods of preventing fluid flow prior to attachment of a fluid fitting.

In operation, after intravascular intervention, the catheter 10 of FIG. 5 is advanced within the patient's blood vessel 32 by conventional means so that the radioisotopic balloon 22' is positioned at a target region 34. The radioisotopic balloon 22' is then inflated with the liquid containing the radioisotope (via shielded injector 38) so it can direct a substantially uniform radiation dose while the matrix 21 allows for release of the radiosensitizer 19 to the target region 34. The radioisotopic balloon 22' is maintained in this inflated state for a predetermined period of time calculated to deliver an effective dosage/concentration of radiation and radiosensitizer to the wall of the blood vessel to inhibit hyperplasia.

Figure 7:
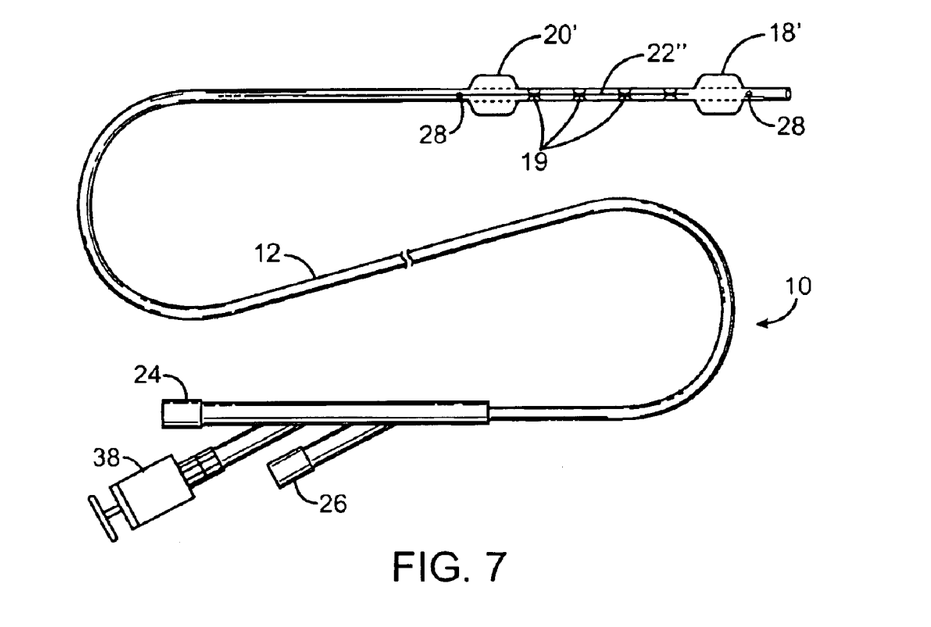
FIG. 7 is a plan view of another alternate embodiment of an apparatus according to the present invention.
Figure 8:
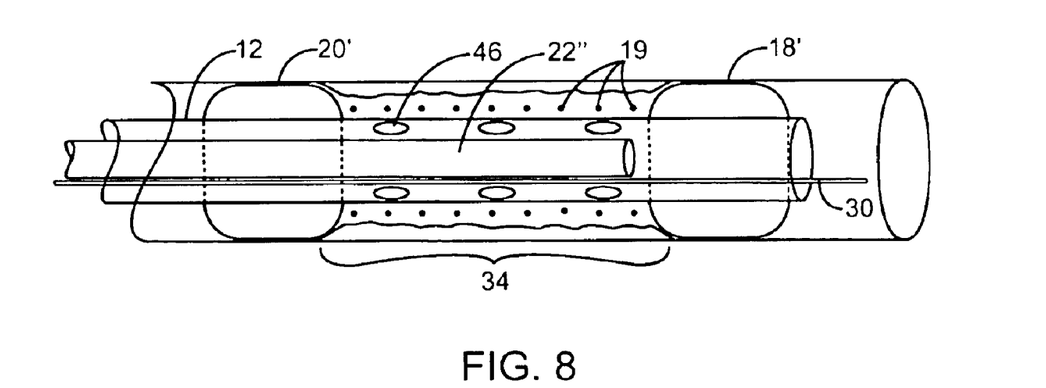
FIG. 8 is a cross sectional view of the apparatus FIG. 7 within a blood vessel.

Referring now to FIGS. 7 and 8, an additional embodiment of the present invention is illustrated. The combined radiation and radiosensitizer delivery catheter 10 for inhibiting hyperplasia comprises a catheter body 12 having an infusion port 46 for releasing a radiosensitizer, a pair of axially spaced apart balloons 18' and 20' on the catheter body 12, and a radiation source 22". The infusion ports 46 are in fluid communication with the guidewire lumen. The radiation source 22" applies a radiation dose between the axially spaced apart balloons 18' and 20' while the infusion ports 46 directly infuse the radiosensitizer 19 therein, as shown in FIG. 8.

Balloons 18' and 20' comprise inelastic or preferably elastic balloons, which are preferably made of polyurethane, Pebax, or other medical grade elastomeric material suitable for constructing puncture-resistant elastic balloons. Balloons 18' and 20' are generally inflatable with a commonly used non-toxic radiopaque contrast medium. Suitable inflation media includes Hexabrix 320™ (sold commercially by Mallinkrodt Corp.) and Iopamiron™ (sold commercially by Schering-Plough Corp.). Contrast media with higher concentrations of the radiopaque material (e.g. iodine) are preferred. It is presently preferred that such a two balloon catheter embodiment be employed in the peripheral arteries as such a structure may help center and correctly position the radiation source 22" in the peripheral vessels, provide a pocket for drug delivery by the infusion ports 46, and aid in uniform radiation dosimetry (which is described in more detail in co-pending U.S. patent application Ser. No. 9/653, 444).

The radiation source 22" depicted in FIG. 7 is a receptacle or lumen 22" in the catheter shaft 12 for receiving radioisotopic materials, like pellets or liquids, and delivering them through the catheter into the wall of a blood vessel. Receptacle 22" illustrates that the radiation source does not have to be an active source integrated into the catheter, but rather can be a receptacle 22" in the catheter for receiving radioisotopic material. The catheter will usually include a radioisotopic inflation lumen to permit introduction and removal of the radioisotopic materials to the receptacle 22".

Several important considerations must be balanced in the design of an apparatus for safely and effectively injecting a radioisotopic material into a patient to irradiate a blood vessel to prevent hyperplasia. Radioisotopic materials may be selected to emit alpha, beta, or gamma radiation. The preferred liquid radioisotopic material will have relatively short half-lives. A shorter half-life is preferred because in the event of a catastrophic failure involving leakage of radioisotopic material into the patient's blood stream, for a given calculated dose, a shorter half life can result in a lesser total body dosage. Radioisotopic material will be selected to provide a total radiation dose in the range from 4 Gray (Gy; 1 Gy=100 rads) to 24 Gy. Suitable emitters of low penetrating radiation for use according the present invention include 90 Strontium, 90 Yttrium, 32 Phosphorus, 125 Iodine, and 103 Palladium. These emitters may be incorporated into or delivered in a solid, liquid, or gaseous form.

In operation, after intravascular intervention, the catheter 10 of FIG. 7 is advanced within the patient's blood vessel 32 by conventional means so that the balloons 18' and 20' are each positioned on an end of a treatment region 34 to isolate the target region. Balloons 18' and 20' are then inflated (via the balloon luer fitting 26) in the blood vessel with non-toxic radiopaque contrast medium until the blood flow past the balloons is substantially stopped (the flow of blood in the vessel itself continues through the perfusion ports 28). Balloons 18' and 20' may also aid in centering the radiation source 22" within the blood vessel lumen as well as act as markers for proper positioning of the distal end 16 of catheter 10 within the treatment region 34 of the blood vessel under fluoroscopy. A radioisotope is then introduced into the receptacle 22" (via shielded injector 38) to the isolated target region to direct a substantially uniform radiation dose over an entire distance between the axially spaced apart balloons 18' and 20'. The radiosensitizer 19 is also released between the first and second balloons 18' and 20' by the infusion ports 46. Balloons 18' and 20' advantageously attenuate radiation from reaching tissue beyond the balloons so as to deliver an effective uniform dose of radiation to the wall of the blood vessel while providing an isolated region or pocket for drug 19 delivery. The radiation and radiosensitizer delivery is carried out for a predetermined period of time calculated to deliver an effective dosage/concentration to the wall of the blood vessel to inhibit hyperplasia.

Figure 9:
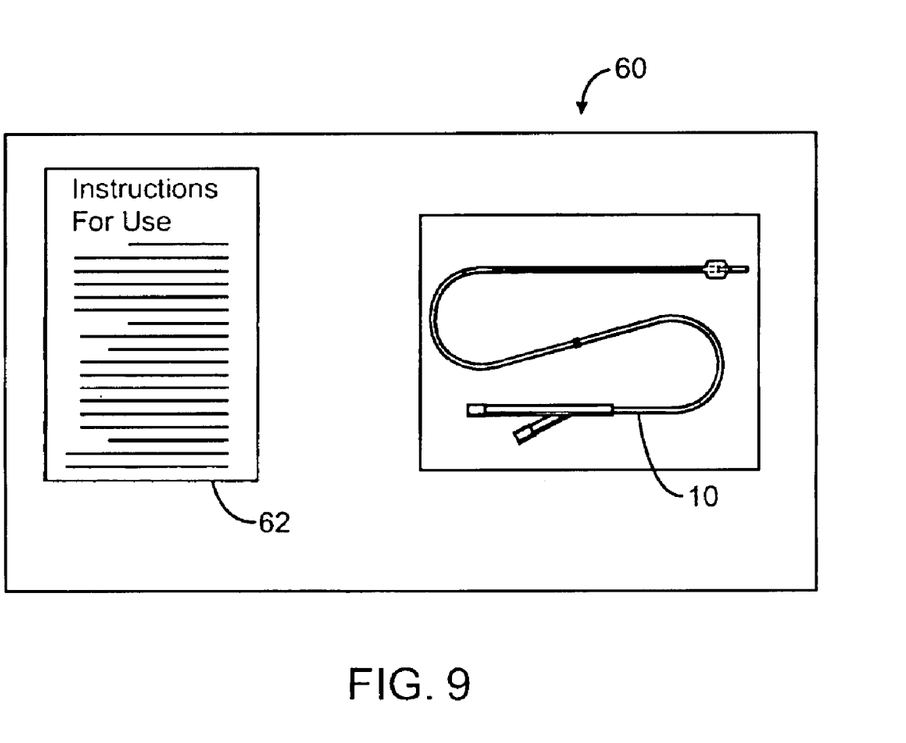
FIG. 9 illustrates a combination radiation and radiosensitizer delivery kit including the apparatus of FIG. 1 and instructions for its use.

Referring now to FIG. 9, this schematic illustrates a kit 60 including a combination radiation and radiosensitizer delivery catheter 10 of FIG. 1 and its instructions for use 62. The combination delivery catheter 10 may be replaced by any of the catheter structures described herein, while the instructions for use 62 will generally recite the steps for performing one or more of the above described methods. The instructions 62 will often be printed, optionally being at least in-part disposed on packaging. The instructions 62 may alternatively comprise a videotape, a CD-ROM or other machine readable code, a graphical representation, or the like showing any of the above described methods.

In general, it will be possible to combine the elements of the differing catheters and treatment methods described above. For example, the catheter of FIG. 1 may comprise a radioisotope radiation source or two microporous balloons for releasing the radiosensitizer. Additionally, the delivery catheter and methods of the present invention may be part of a catheter that combines balloon angioplasty and/or other interventional treatments, like stent placement, with the presently claimed radiation and radiosensitizer delivery catheter.

Although certain preferred embodiments and methods have been disclosed herein, it will be apparent from the foregoing disclosure to those skilled in the art that variations and modifications of such embodiments and methods may be made without departing from the true spirit and scope of the invention. Therefore, the above description should not be taken as limiting the scope of the invention which is defined by the appended claims.

What is claimed is:

1. A combined radiation and drug delivery catheter for inhibiting hyperplasia, comprising:
    a catheter body having a proximal end and a distal end;
    an ionizing radiation source coupleable to the catheter body for applying a radiation dose to a body lumen;
    a source of at least one radiosensitizer;
    a balloon coupleable to the catheter body; and
    a matrix formed over at least a portion of the balloon for releasing the radiosensitizer to the body lumen, wherein the radiosensitizer source is in or beneath the matrix and the balloon is free of the radiosensitizer source, wherein the matrix is not inflatable independent of the balloon, and wherein the combined radiation and radiosensitizer delivery catheter inhibit hyperplasia.

2. A delivery catheter as in claim 1, wherein the ionizing radiation source is an x-ray tube.

3. A delivery catheter as in claim 1, wherein the ionizing radiation source is a radioisotope.

4. A delivery catheter as in claim 1, wherein the ionizing radiation source is a receptacle in the catheter body for receiving radioisotopic materials.

5. A delivery catheter as in claim 1, wherein the source of at least one radiosensitizer is selected from the group consisting of taxol, misonidazole, metronidazole, etanidazole, 5-fluorouracil, texaphyrin, C225, and cyclooxygenase-2 inhibitor.

6. A delivery catheter as in claim 1, wherein the source of at least one radiosensitizer comprises a source of taxol incorporated in a solution with polyoxyethylated castor oil and dehydrated alcohol.

7. A delivery catheter as in claim 1, wherein the radiosensitizer is attached or encapsulated in a lipid or surfactant carrier.

8. A delivery catheter as in claim 1, wherein the matrix comprises a rate controlling material, wherein the rate controlling material controls the rate at which the radiosensitizer is released from or through the matrix.

9. A delivery catheter as in claim 8, wherein the radiosensitizer is released from the matrix by diffusion through the matrix.

10. A delivery catheter as in claim 8, wherein the radiosensitizer is released from the matrix by degradation of the matrix.

11. A delivery catheter as in claim 8, wherein the rate controlling material is porous and the radiosensitizer is released from the material by elution from pores.

12. A delivery catheter as in claim 1, wherein the radiosensitizer is disposed on the balloon.

13. A delivery catheter as in claim 1, wherein the ionizing radiation source is positionable within the balloon.

14. A delivery catheter as in claim 1, further comprising perfusion threading on an outer surface of the balloon.

15. A delivery catheter as in claim 14, wherein the threading has a spiral, helical, or angled pattern.

16. A delivery catheter as in claim 1, wherein the catheter body has a perfusion lumen.

17. A combined radiation and drug delivery catheter for inhibiting hyperplasia, comprising:
    a catheter body having a proximal end and a distal end;
    an ionizing radiation source coupleable to the catheter body for applying a radiation dose to a body lumen;
    a source of at least one radiosensitizer;
    means coupleable to the catheter body or the radiation source for releasing the radiosensitizer to the body lumen, wherein the combined radiation and radiosensitizer delivery catheter inhibit hyperplasia; and
    perfusion threading on an outer surface of the means for releasing the radiosensitizer.

18. A delivery catheter as in claim 17, wherein the ionizing radiation source is an x-ray tube.

19. A delivery catheter as in claim 17, wherein the source of at least one radiosensitizer is selected from the group consisting of taxol, misonidazole, metronidazole, etanidazole, 5-fluorouracil, texaphyrin, C225, and cyclooxygenase-2 inhibitor.

20. A delivery catheter as in claim 17, wherein the source of at least one radiosensitizer comprises a source of taxol incorporated in a solution with polyoxyethylated castor oil and dehydrated alcohol.

21. A delivery catheter as in claim 17, wherein the radiosensitizer is attached or encapsulated in a lipid or surfactant carrier.

22. A delivery catheter as in claim 17, wherein the means for releasing the radiosensitizer comprises a microporous balloon on the catheter body.

23. A delivery catheter as in claim 22, wherein the microporous balloon contains the radiosensitizer and the radiosensitizer is released from the microporous balloon by elution from pores.

24. A delivery catheter as in claim 23, wherein the microporous balloon is inflatable with the radiosensitizer.

25. A delivery catheter as in claim 17, wherein the means for releasing the radiosensitizer comprises a matrix formed over at least a portion of a balloon on the catheter body, wherein the radiosensitizer is in or beneath the matrix.

26. A delivery catheter as in claim 25, wherein the matrix comprises a rate controlling material, wherein the rate controlling material controls the rate at which the radiosensitizer is released from or through the matrix.

27. A delivery catheter as in claim 26, wherein the radiosensitizer is released from the matrix by diffusion through the matrix.

28. A delivery catheter as in claim 26, wherein the radiosensitizer is released from the matrix by degradation of the matrix.

29. A delivery catheter as in claim 26, wherein the rate controlling material is porous and the radiosensitizer is released from the material by elution from pores.

30. A delivery catheter as in claim 25, wherein the radiosensitizer is disposed on the balloon.

31. A delivery catheter as in claim 17, wherein the ionizing radiation source is positionable within the balloon.

32. A delivery catheter as in claim 17, wherein the threading has a spiral, helical, or angled pattern.

* * * * *